US00PP19686P2

(12) United States Plant Patent
Lamb et al.

(10) Patent No.: US PP19,686 P2
(45) Date of Patent: Feb. 10, 2009

(54) ***ANTHURIUM* PLANT NAMED 'TWYANBD9'**

(50) Latin Name: *Anthurium hybrida*
Varietal Denomination: TWYANBD9

(75) Inventors: Ann E. Lamb, Sebring, FL (US); Marianne E. Knauss, Longwood, FL (US)

(73) Assignee: Kerry's Bromeliad Nursery, Inc., Apopka, FL (US)

( * ) Notice: Subject to any disclaimer, the term of this patent is extended or adjusted under 35 U.S.C. 154(b) by 0 days.

(21) Appl. No.: 11/906,885

(22) Filed: Oct. 4, 2007

(51) Int. Cl.
*A01H 5/00* (2006.01)

(52) U.S. Cl. ..... Plt./369
(58) Field of Classification Search ..... Plt./369, Plt./365
See application file for complete search history.

*Primary Examiner*—Annette H Para
*Assistant Examiner*—S. B McCormick Ewoldt
(74) *Attorney, Agent, or Firm*—Jondle & Associates, P.C.

(57) ABSTRACT

A new *Anthurium* plant particularly distinguished by having medium to large, triangular, red-pink, shiny spathes, contrasting, firm/leathery, very shiny, dark metallic leaves that become very dark green as they mature, and a dense, upright, branched, leafy growth habit, is disclosed.

1 Drawing Sheet

Genus and species: *Anthurium hybrida.*
Variety denomination: 'TWYANBD9'.

BACKGROUND OF THE NEW PLANT

The present invention comprises a new and distinct cultivar of *Anthurium,* botanically known as *Anthurium hybrid,* and hereinafter referred to by the cultivar name 'TWYANBD9'. The new cultivar originated from a hybridization made in 2003 in Apopka, Fla., USA. The female parent was the *Anthurium* plant, 'Pink Paradise' (U.S. Plant Pat. No. 11,657), while the male parent was the proprietary *Anthurium* plant 'H-43' (unpatented).

The new cultivar was selected in March 2005 from the results of the hybridization and has been asexually reproduced repeatedly by tissue culture in Apopka, Fla., USA over a two and one-half year period. The present invention has been found to retain its distinctive characteristics through successive asexual propagations.

SUMMARY OF THE INVENTION

The following are the most outstanding and distinguishing characteristics of this new cultivar when grown under normal horticultural practices in Apopka, Fla.

1) Medium to large, triangular, red-pink, shiny spathes;
2) Contrasting, firm/leathery, very shiny, dark metallic leaves which become very dark green as they mature; and
3) Dense, upright, branched, leafy growth habit.

DESCRIPTION OF PHOTOGRAPH

This new *Anthurium* plant is illustrated by the accompanying photograph which shows the overall plant habit including blooms, buds and foliage of the plant. The colors shown are as true as can be reasonably obtained by conventional photographic procedures. The photograph is of a 24-month old plant grown in a greenhouse in Apopka, Fla.

DESCRIPTION OF THE NEW CULTIVAR

The following detailed description sets forth the distinctive characteristics of 'TWYANBD9'. The data which define these characteristics were collected from asexual reproductions carried out in Apopka, Fla. The plant history was taken on 24-month old plants which were planted from tissue culture in 25-cm pots and grown in a greenhouse with average daily temperatures of 85° F.–95° F. and average nightly temperatures of 72° F. to 78° F. Observations were made in March 2007. Color readings were taken under natural light in the greenhouse. Color references are primary to The R.H.S. Colour Chart of The Royal Horticultural Society of London (R.H.S.) (2001).

DETAILED BOTANICAL DESCRIPTION

Classification:
- *Family.*—Aracea.
- *Botanical.—Anthurium hybrida.*
- *Common.—Anthurium.*

Parentage:
- *Female parent.—Anthurium* plant 'Pink Paradise' (U.S. Plant Pat. No. 11,657) with pink spathes.
- *Male parent.—Anthurium* plant 'H-43' (unpatented) with dark-red spathes.

Growth:
- *Form.*—Upright, symmetrical, with outward pointed leaves; plant wider than tall.
- *Growth and branching habit.*—Upright stems, dense, branched habit (basal, axillary branching), with many leaves and flowers; vigorous growth habit, plant produces numerous branches, leaves and flowers.
- *Height* (*measured from soil to top of canopy*).—50 cm to 56 cm
- *Height* (*measured from soil to top of inflorescences.*).—56 cm to 71 cm (flowers at, among and above the top of the foliage).
- *Width* (*area of spread*).—70 cm to 80 cm.

*Time to produce a finished flowering plant.*—Single micro cutting to liner: 14 to 16 weeks. 10 cm pot from liner: 7 to 8 months (first flowers). 15 cm pot from liner: 10 to 12 months. 20 cm pot from liner: 14 months.

*Growth rate.*—Typical of commercial *Anthurium* cultivars

*Root description.*—Thick fleshy roots with finer laterals; between RHS 197B to RHS 197C; RHS 182D where exposed to light; RHS 152D root tips.

*Durability of foliage stresses.*—Durable, holds up well under typical commercial practice; large leaves are prone to physical damage or tearing.

*High temperature tolerance.*—To about 104° F. without damage.

*Low temperature tolerance.*—To about 55° F. without damage.

Stems:

*Number of stems per plant.*—12.

*Length (from soil line to the junction of the last two unrolled leaves).*—11 cm.

*Diameter (measured from about 6 cm above the soil surface).*—1.3 cm.

*Internode length.*—1.3 cm.

*Color.*—Immature: Between RHS 145B to RHS 145C sheathed with between RHS 144B to RHS 144C (green) cataphylls. Mature: RHS 146D sheathed with RHS 200B dried brown cataphylls.

*Appearance.*—Upright, cylindrical, round, thick with regularly spaced petioles and short internodes; cataphylls are present and non-persistent; surface is smooth and glossy.

*Pubescence.*—Absent.

*Aspect.*—Upright.

*Strength.*—Sturdy, tough, upright.

*Cataphylls.*—Shape and arrangement: Lanceolate, acute, keeled; base of cataphyll clasps the stem. Length: 7.9 cm to 13.0 cm. Width: 3.5 cm (flattened). Texture: Inside: Shiny, smooth. Outside: Glossy. Color: Between RHS 144B to RHS 144C; becoming RHS 200B with senescence.

Leaves:

*Arrangement and type.*—Alternate, simple, single leaf per petiole; midrib on lower surface is keeled.

*Quantity of leaves per stem.*—6 per main stem; fewer leaves on younger axillary branches.

*Length.*—25 cm to 34 cm.

*Width (natural).*—14 cm to 15.5 cm.

*Width (flattened).*—16 cm to 18 cm.

*Shape.*—Ovate.

*Apex.*—Acuminate, mucronate.

*Base.*—Cordate.

*Margin.*—Entire, with some broad undulations; leaf blade flat or somewhat folded upward lengthwise.

*Appearance (both surfaces).*—Smooth, medium thickness, rigid, firm/leathery, very shiny/metallic sheen, dulling with age.

*Pubescence (on both surfaces).*—Absent.

*Immature leaf color.*—Upper surface: Between RHS N186A to RHS 202A. Lower surface: Between RHS 200B to RHS 200C.

*Mature leaf color.*—Upper surface: Darker and greener than, but closest to RHS 147A often tinged with RHS N186A. Lower surface: Between RHS 146A to RHS N199A.

*Venation.*—Pinnate. Venation color: Upper surface: Immature: Same as surrounding tissue Immature midrib: Between RHS 200C to RHS 200D Mature: Between RHS 147C to RHS N199A Mature midrib: RHS 147B often tinged with colors between RHS 200C to RHS 200D. Lower surface: Immature: RHS 187A Immature midrib: Between RHS 183A to RHS 183B Mature: RHS 147C often tinged with RHS N199A Mature midrib: Between RHS 146C to RHS 146D often tinged with RHS 182B.

*Petiole.*—Aspect: Vertical and upright when newly emerged, becoming about 35° to 45° from the vertical axis with maturity. Length (from base of leaf to junction of petiole and stem): 37 cm to 46 cm. Diameter: Distal (measured in the center below the geniculum and above the petiole wing tip): 0.40 cm. Proximal: 0.11 cm. Color: Immature: Between RHS 200B to RHS N186C. Mature: RHS 146C tinged with RHS N186C.

*Geniculum.*—Length: 1.7 cm to 2.4 cm. Diameter: 0.45 cm. Aspect: Straight or curved outward. Color: Immature: Between RHS 200B to RHS N186C. Mature: RHS 146C tinged with RHS N186C.

*Wing.*—Length: 4.0 cm (tip of wing acute or flush with petiole). Diameter: 0.9 cm. Color: Between RHS 145B to RHS 145C.

Inflorescence:

*Arrangement.*—Spathe/spadix atop peduncle, emerges from petiole sheath; peduncle attached to stem at leaf axil; inflorescences mostly clustered along the center of the plant; persistent.

*Aspect.*—Upright straight, vertical when newly emerged, leaning outward somewhat with age.

*Height.*—56 cm to 71 cm.

*Depth.*—Spathe folded upward lengthwise 3.5 cm to 7.0 cm deep.

*Flowering habit and season.*—Continuous flowering year round, but most prolific in winter and spring.

*Number of inflorescences per plant.*—18 inflorescences and buds.

*Buds.*—Shape is lanceolate, length is 5.2 cm to 11.5 cm, width is 0.8 cm to 1.7 cm, color is RHS 51A while the proximal end is often tinged with colors between RHS 53A to RHS 53B and the apex is tinged with RHS 150C.

*Fragrance.*—Absent.

*Rate of inflorescence opening.*—About every 14 days, 2 to 3 new inflorescences emerge.

*Longevity on plant.*—About 6 plus weeks.

*Longevity as cut flower.*—3 to 4 weeks.

Spathe:

*Appearance.*—Medium to large sized, triangular, red-pink, shiny, margins fold upward lengthwise; very shiny when immature, becoming glossy with age, medium thickness, firm/leathery, slightly concave between veins.

*Arrangement/aspect.*—Typically horizontal and often curved downward somewhat distally.

*Pubescence (on both surfaces).*—Absent.

*Shape.*—Broadly ovate, triangular.

*Margin.*—Entire, with some broad undulations.

*Apex.*—Acute to acuminate, mucronate.

*Base.*—Cordate to truncate.

*Longevity.*—6 plus weeks with good color.

*Size.*—Length: 12.0 cm to 20 cm. Width (natural): 8.0 cm to 10 cm. Width (flattened): 9.2 cm to 19.0 cm.

*Color.*—When opening: Front side: Very shiny between RHS 53B to RHS 53C with RHS 55C primary veins and RHS 55C around the base of the spadix. Rear side: Between RHS 51A to RHS 51B. Fully opened: Front side: RHS 53B with lighter veins of between RHS 54B to RHS 54C; lobes often prominently marked with colors between RHS 147A to RHS 146A (green) especially if plant is mature. Rear side: Between RHS 47B to RHS 47C, lobes and apex. marked with colors between RHS 147A to RHS 146A (green) Fading to: RHS 146B with areas of RHS 183D and RHS 181B.

Spadix:

*Appearance.*—Columnar, upright, affixed atop very short stipe at junction of peduncle and spathe.

*Arrangement/aspect.*—Upright, near vertical, or tilted outward.

*Shape.*—Columnar, narrower, tapered at tip; apex bluntly rounded.

*Margin.*—Round in transverse section.

*Apex.*—Bluntly rounded, obtuse.

*Base.*—Bluntly rounded.

*Size.*—Length: 4.8 cm to 6.6 cm. Diameter: 0.7 cm.

*Color (immature).*—Proximal: RHS 65C. Distal: RHS 33C.

*Color (mature).*—Between RHS 65C to RHS 65D tinged with RHS 186D.

Flowers:

*Arrangement.*—Flowers reduced, tightly packed on spadix.

*Type.*—Bisexual, reduced, minuscule; female flowers receptive first, followed by male flowers.

*Shape.*—Individual flowers roughly pyramidal in shape, tightly packed on the spadix; flowers sessile on spadix; face of individual flower flat and square or diamond shaped; pistil in center, protruding, surrounded by anthers; four triangular tepals at corners.

*Diameter.*—0.22 cm.

*Height.*—0.3 cm from base to tip of pistil; stigma protrudes about 0.08 cm when receptive.

*Number of female flowers per spadix.*—280.

*Number of male anthers per flower.*—About 8 (minuscule; not clearly visible).

Peduncle:

*Length.*—45 cm to 58 cm.

*Diameter.*—0.30 cm to 0.60 cm.

*Angle.*—Straight, upright or curved outward.

*Strength.*—Sturdy, somewhat flexible.

*Color.*—Immature: Between RHS 200B to RHS N186C. Mature: RHS 146C often variably tinged with RHS N186C.

Reproductive organs:

*Anther color.*—Same as surrounding spadix tissue.

*Pollen amount.*—None.

*Stigma color.*—Between RHS 65C to RHS 65D.

*Ovary color.*—Between RHS 65C to RHS 65D.

Fruit and Seed Set: Seed production has not been observed to date.

Disease and insect resistance: No particular resistance or susceptibility different from other *Anthurium* varieties.

COMPARISON WITH PARENTAL AND COMMERCIAL CULTIVARS

'TWYANBD9' differs from the female parent *Anthurium* plant 'Pink Paradise' (U.S. Plant Pat. No. 11,657), by having narrower, shiny, red-pink spathes, while 'Pink Paradise' has very large, cordate pink spathes and lobes flushed with green. 'TWYANBD9' has immature leaves that are very dark with a metallic sheen and become dark-green with maturity, while 'Pink Paradise' has uniformly green leaves. 'TWYANBD9' has an upright, highly branched growth habit with outward pointing leaves, while 'Pink Paradise' has an upright, symmetrical and clumping growth habit that is less dense and has fewer basal branches.

'TVMANBD9' differs from the male parent *Anthurium* plant 'H-43' (unpatented) by having larger, shiny, red-pink spathes, while 'H-43' has smaller, shiny, very dark-red spathes. 'TWYANBD9' has an upright branched growth habit with outward pointing leaves, while 'H-43' has an upright, rounded growth habit that is less dense with fewer basal branches and larger leaves. In addition, 'TYWANBD9' is more tolerant of adverse conditions, while 'H-43' has spathes and foliage that tend to fade if the plant is exposed to high temperatures.

'TWYANBD9' differs from the commercial variety 'Pippi' (U.S. Plant Pat. No. 14,475), by having larger spathes that fold upward lengthwise, while 'Pippi' has smaller, flatter spathes. 'TWYANBD9' has shiny, red-pink spathes that are often tinged with green at the base, while 'Pippi' has uniformly red spathes that are not as shiny. In addition, 'TWYANBD9' has immature leaves that are very dark with a metallic sheen and become dark-green with maturity, while 'Pippi' has immature leaves that are green with darker veins.

'TWYANBD9' differs from the co-pending anthurium application 'TWYANBD18' (U.S patent application Ser. No. 11/906,501) in that 'TWYANBD9' has larger spathes (length is 12.0 cm to 20.0 cm and width is 8.0 cm to 10.0 cm) than 'WYANBD18' (length is 7.5 cm to 11.5 cm and width is 5. cm to 7.5 cm). Additionally, 'TWYANBD9' has longer peduncles (45.0 cm to 58.0 cm) than 'TWYANBD18' (45.0 cm).

I claim:

1. A new and distinct cultivar of *anthurium* plant as shown and described herein.

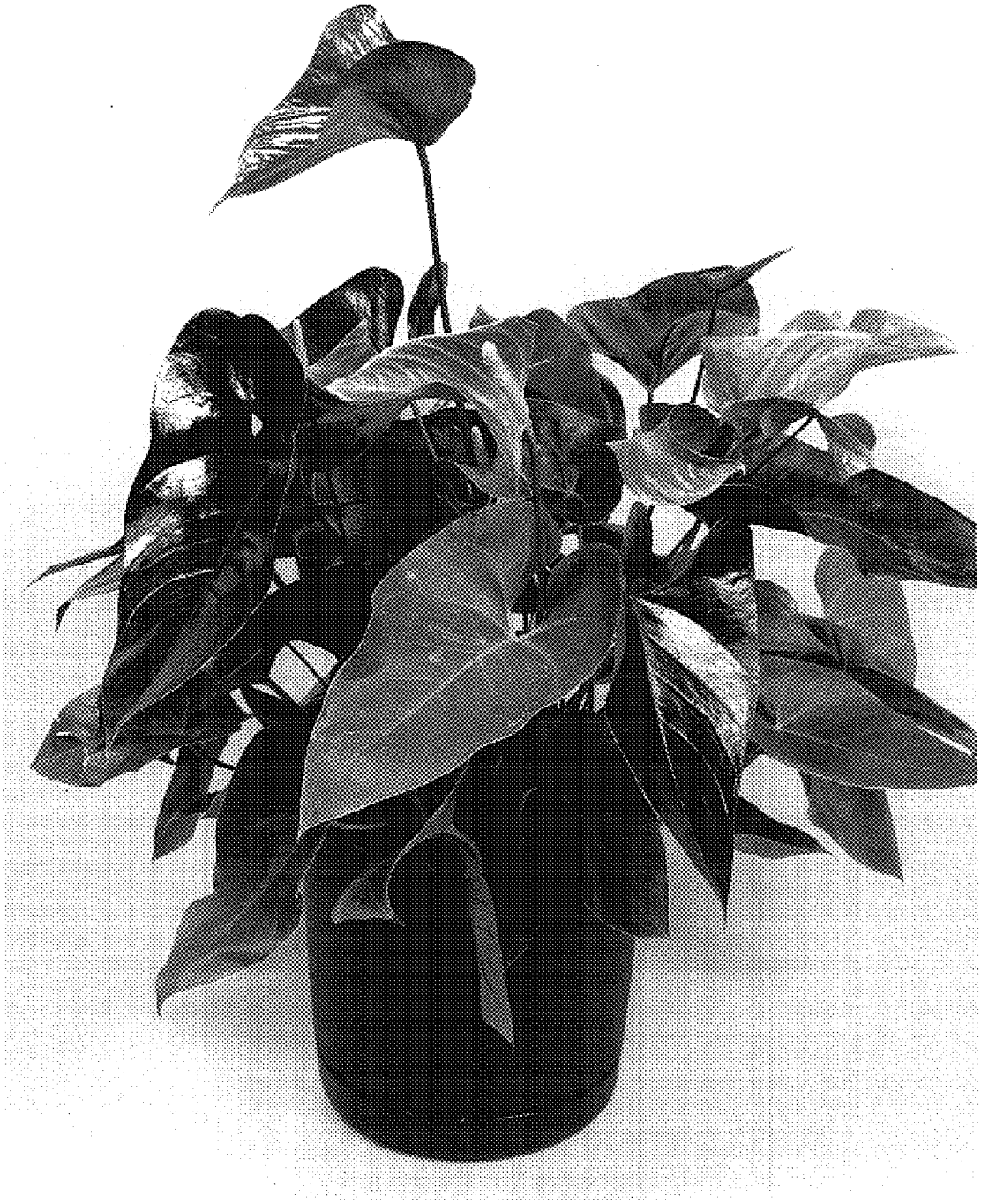

* * * * *